US009386918B2

(12) United States Patent
Ammari et al.

(10) Patent No.: US 9,386,918 B2
(45) Date of Patent: Jul. 12, 2016

(54) OPHTHALMIC SURGICAL SYSTEM WITH BLUE LIGHT FILTERING

(71) Applicant: Novartis AG, Basel (CH)

(72) Inventors: Eyad Ammari, Lake Forest, CA (US); Steven T. Charles, Lake Forest, CA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/309,653

(22) Filed: Jun. 19, 2014

(65) Prior Publication Data

US 2015/0366446 A1    Dec. 24, 2015

(51) Int. Cl.
| | |
|---|---|
| *A61B 3/00* | (2006.01) |
| *G02B 5/20* | (2006.01) |
| *G02B 26/00* | (2006.01) |
| *A61F 9/007* | (2006.01) |

(52) U.S. Cl.
CPC .............. *A61B 3/0008* (2013.01); *A61F 9/007* (2013.01); *G02B 5/201* (2013.01); *G02B 26/008* (2013.01)

(58) Field of Classification Search
CPC ........ A61B 3/0008; A61B 3/12; A61B 3/135; A61B 3/14; A61B 3/13; A61B 1/0646; A61B 1/0661; G02B 26/008; G02B 26/023; G02B 27/149; G02B 27/144; G02B 27/145; G02B 27/1046; G02B 27/1006
USPC .............. 600/249, 160; 606/4; 362/572, 232, 362/269, 277, 282; 351/221, 205, 206, 210, 351/211, 216, 220, 209
See application file for complete search history.

(56) References Cited

U.S. PATENT DOCUMENTS

| | | | | | |
|---|---|---|---|---|---|
| 6,309,070 | B1 * | 10/2001 | Svetliza | ............... | A61B 3/1225 351/221 |
| 7,654,716 | B1 * | 2/2010 | Bhadri | ..................... | A61B 3/13 362/232 |
| 2006/0268231 | A1 * | 11/2006 | Gil | .......................... | A61B 3/12 351/221 |
| 2010/0261966 | A1 * | 10/2010 | Reimer | ................ | A61B 1/0646 600/160 |
| 2012/0083772 | A1 * | 4/2012 | Rubinfeld | ............. | A61F 9/0079 606/4 |

OTHER PUBLICATIONS

International Search Report and Written Opinion issued for PCT/US2015/030584, dated Aug. 14, 2015, 9 pgs.

* cited by examiner

*Primary Examiner* — Pedro Philogene
(74) *Attorney, Agent, or Firm* — Haynes and Boone, LLP

(57) ABSTRACT

An ophthalmic surgical system can include a light source configured to generate a light beam and a filter wheel disposed between the light source and an intraocular illumination device. The filter wheel can include an unfiltered area, a first filtered area, and a second filtered area. The first and second filtered areas can limit transmission of certain wavelengths of the light beam to the intraocular illumination device. The system can include an actuator configured to selectively move the filter wheel to cause the light beam to pass through the unfiltered area, the first filtered area, and/or the second filtered area. The system can include a computing device configured to provide a control signal to the actuator. The computing device can be configured to provide a control signal to the actuator based on a beam location, a beam composition, an exposure time, and/or a limited visibility condition.

19 Claims, 5 Drawing Sheets

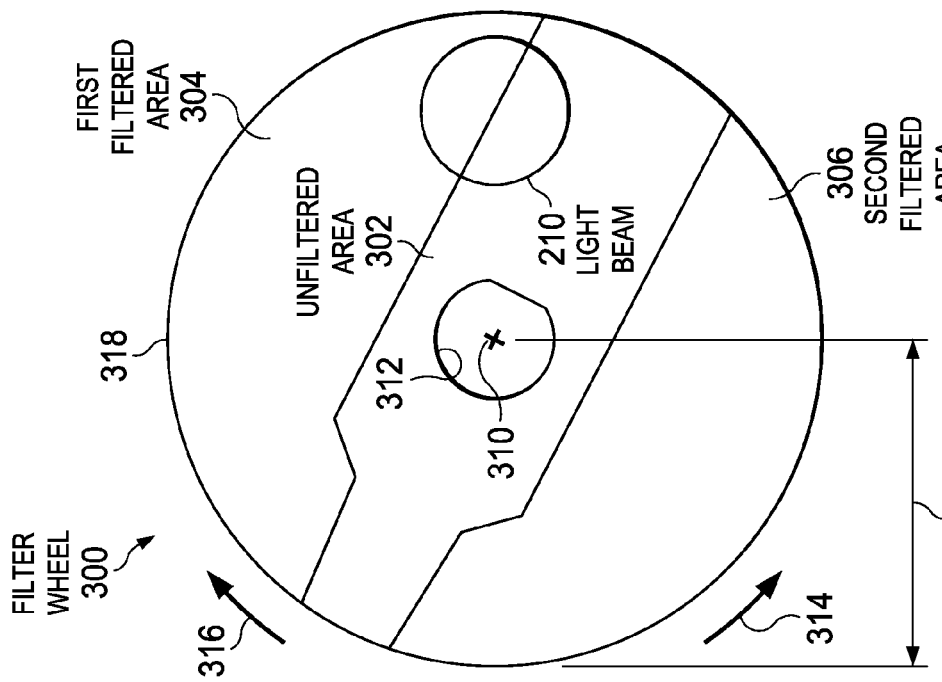
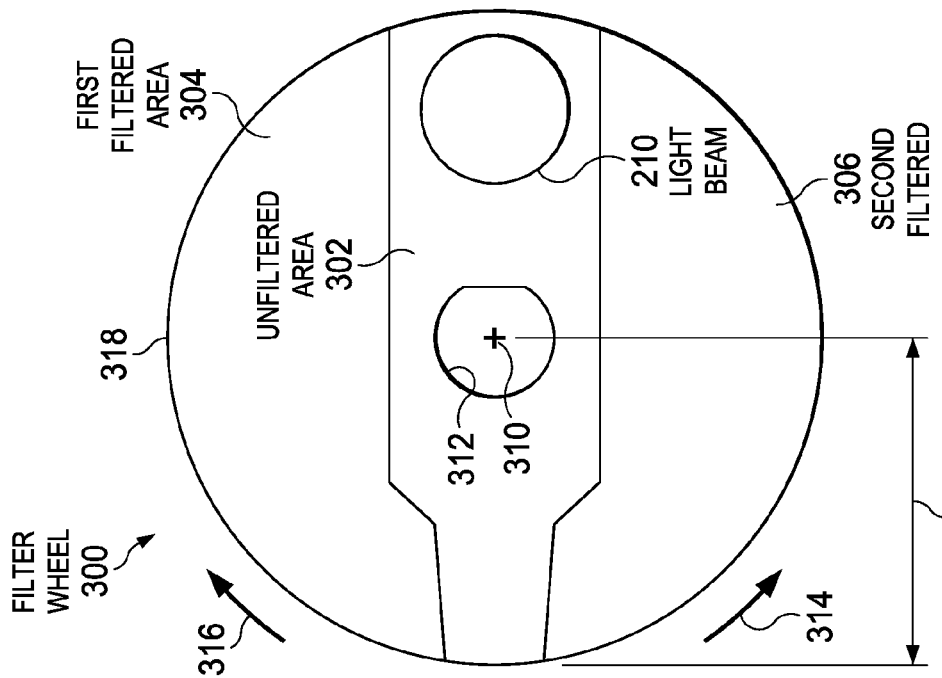

OPHTHALMIC SURGICAL SYSTEM WITH BLUE LIGHT FILTERING

BACKGROUND

1. Technical Field

Embodiments disclosed herein are related to improved illumination for vitreo-retinal, macular, or other ophthalmic surgeries. More specifically, embodiments described herein relate to ophthalmic surgical systems including an illumination system with blue light filtering to reduce the risk of phototoxicity.

2. Related Art

Ophthalmic surgical procedures, such as vitreo-retinal surgeries, can involve illumination of relevant anatomy in a patient's eye. For example, light can be directed at the macula during a vitrectomy. Illumination can be provided by one or more illuminators, such as an endoillumination probe.

Providing illumination within the eye can be challenging for several reasons. For example, exposure to light associated with wavelengths in the blue region of the visible spectrum can be harmful to the eye. Shorter wavelength light has greater energy per photon and is therefore more likely to cause phototoxicity than longer wavelength light. The standardized metric for retinal phototoxicity is the Aphakic Hazard. The eye can handle some amount of blue light without adverse effects, but if the duration of the surgery extends beyond a certain time, a surgeon must take steps to avoid harm to the eye. Conventionally, these steps include lowering the intensity of the light in the eye. This, however, can require the surgeon to work in a darker environment than desired for the duration of the surgical procedure—circumstances that can make successful completion of the procedure more difficult.

More recently, illumination systems have been developed that allow a surgeon to eliminate wavelengths associated with blue light. In these systems, a surgeon has two choices: include blue light or exclude blue light. This too, however, can be problematic because the surgical field appears yellow with the removal of blue light. Such working conditions are not ideal for a surgeon to successfully complete the surgical procedure.

Accordingly, there remains a need for improved devices, systems, and methods that facilitate intraocular illumination with improved blue light filtering by addressing one or more of the needs discussed above.

SUMMARY

The presented solution fills an unmet medical need with a unique solution to provide intraocular illumination during ophthalmic surgical procedures with selective filtering of one or more wavelength ranges associated with blue light.

Consistent with some embodiments, an ophthalmic surgical system can include: a light source configured to generate a light beam; a filter wheel disposed between the light source and an intraocular illumination device, the filter wheel including an unfiltered area, a first filtered area configured to limit the transmission of a first range of wavelengths of the light beam to the intraocular illumination device, and a second filtered area configured to limit the transmission of a second range of wavelengths of the light beam to the intraocular illumination device; and an actuator configured to selectively move the filter wheel to cause the light beam to pass through at least one of the unfiltered area, the first filtered area, and the second filtered area of the filter wheel.

Consistent with some embodiments, an ophthalmic filter wheel for filtering a light beam of an intraocular illumination device can include: an unfiltered area; a first filtered area configured to limit the transmission of a first range of wavelengths of the light beam to the intraocular illumination device; and a second filtered area configured to permit the transmission of a second range of wavelengths of the light beam to the intraocular illumination device, wherein the unfiltered area is positioned adjacent to at least one of the first and second filtered areas.

Consistent with some embodiments, a method of performing an ophthalmic surgical procedure can include: guiding a light beam through a filter wheel to an intraocular illumination device, wherein the filter wheel includes an unfiltered area, a first filtered area configured to limit the transmission of a first range of wavelengths of the light beam to the intraocular illumination device, and a second filtered area configured to limit the transmission of a second range of wavelengths of the light beam to the intraocular illumination device; and selectively moving the filter wheel to cause the light beam to pass through at least one of the unfiltered area, the first filtered area, and the second filtered area of the filter wheel.

Additional aspects, features, and advantages of the present disclosure will become apparent from the following detailed description.

BRIEF DESCRIPTION OF THE DRAWINGS

FIG. 3a provides a diagram illustrating an ophthalmic filter wheel.

FIG. 3b provides a diagram illustrating an ophthalmic filter wheel.

Figure 1:
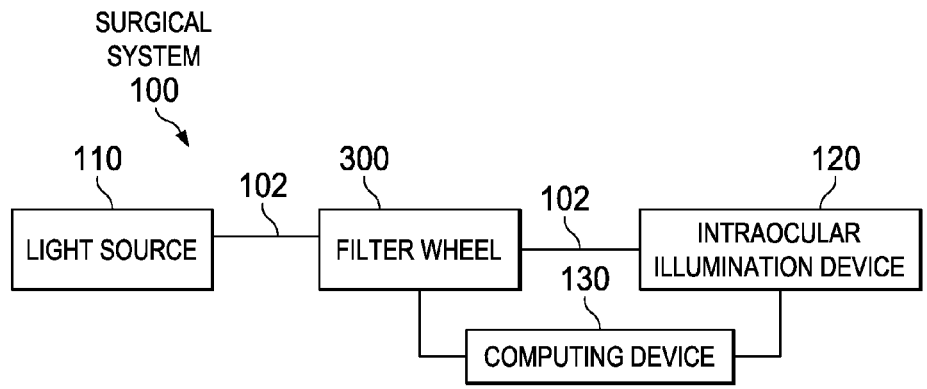
FIG. 1 provides a diagram illustrating an ophthalmic surgical system.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

The ophthalmic surgical systems of the present disclosure can include a light filtering system using a filter wheel introduced into a beam path of a fiber-based illuminator. The filter wheel can have two sections that attenuate different wavelength ranges of light and a clear section that allows substantially all wavelengths to pass through unimpeded. The filter wheel can be moved into the beam path to provide filtering of one or more wavelength ranges associated with blue light.

The filter wheel can also allow for light to pass through unimpeded and to pass through with concurrent filtering in multiple wavelength ranges.

The ophthalmic surgical systems including the filter wheel of the present disclosure can provide numerous advantages, including (1) improved patient safety by reducing the risk of phototoxicity and the Aphakic Hazard metric; (2) optimized control of blue light filtering based on the target area in the eye; (3) optimized control of the percentage of blue light allowed to pass through to the eye; (4) optimized control of blue light exposure time to the eye; (5) optimized control of illumination during the surgical procedure based on a patient's physiological conditions that limit a surgeon's ability to see relevant anatomy within the eye; (6) improved working conditions for a surgeon during the ophthalmic surgical procedure; (7) selective, incremented, and/or gradated blue light filtering; (8) attenuation and/or elimination of multiple wavelength ranges associated with blue light; and (9) relatively simple and cost-effective implementation.

Figure 2A:
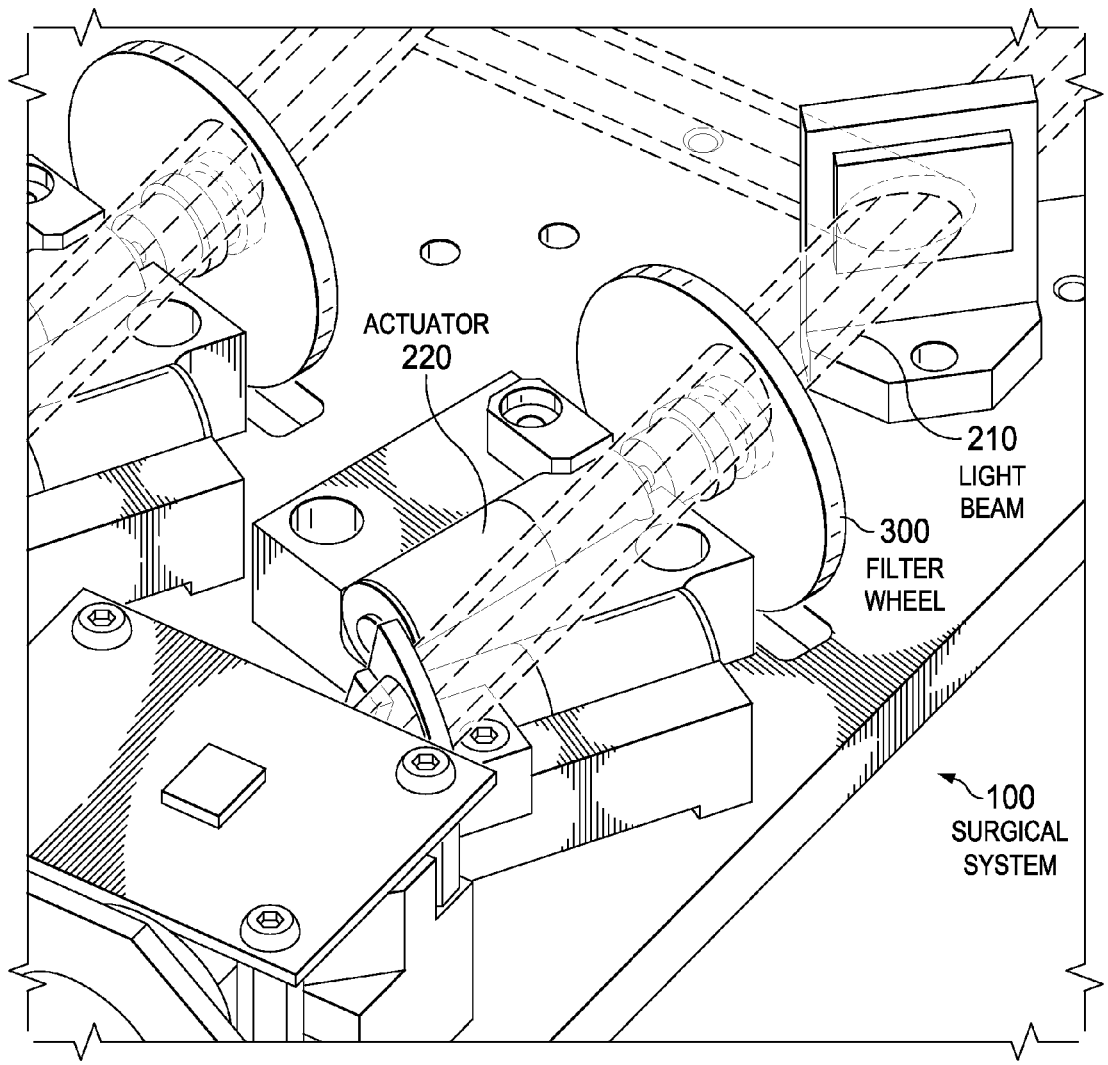
FIG. 2a provides a diagrammatic perspective view of a portion of an ophthalmic surgical system.
Figure 2B:
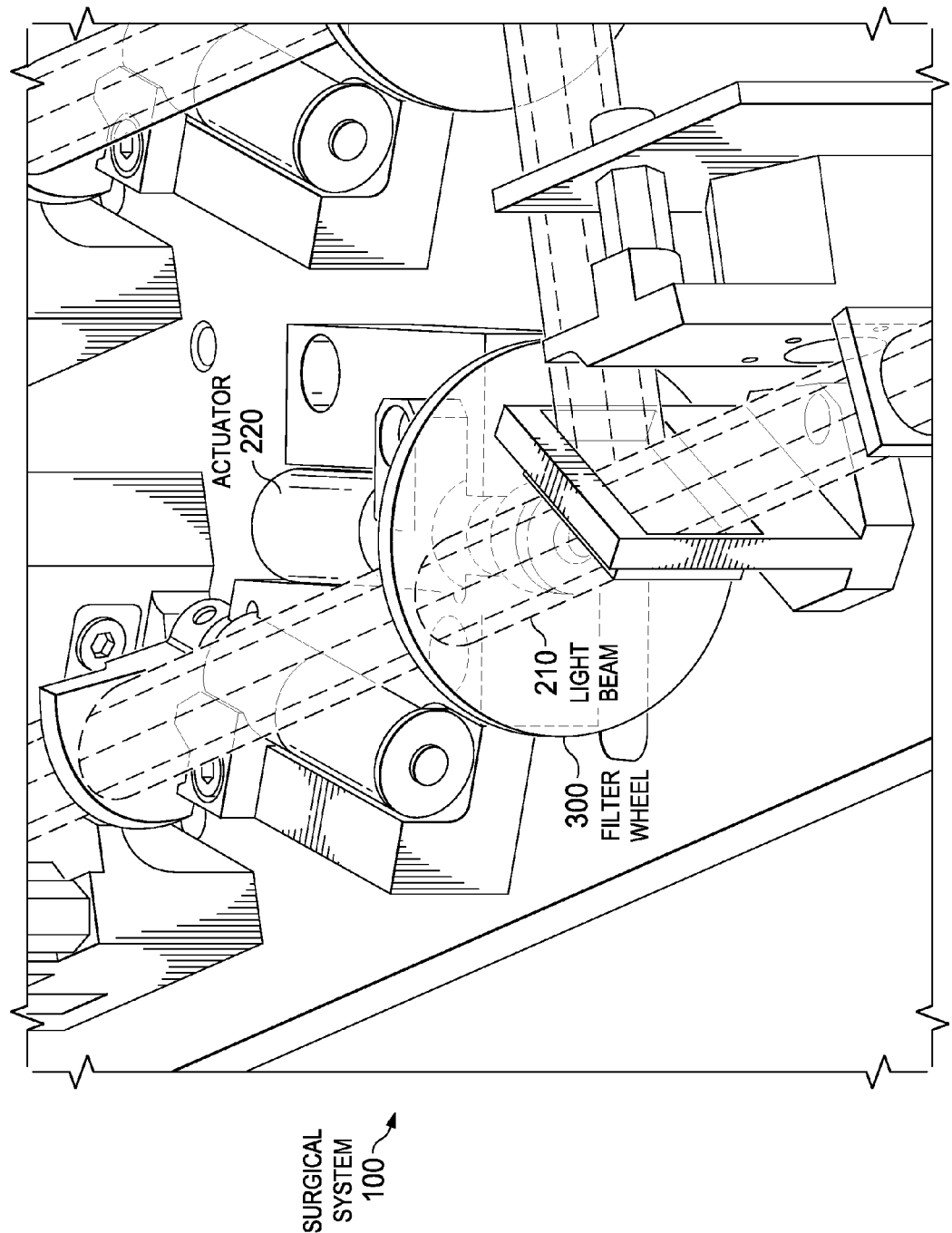
FIG. 2b provides a diagrammatic perspective view of a portion of an ophthalmic surgical system.

FIG. 1 illustrates an ophthalmic surgical system 100. The ophthalmic surgical system 100 can include a light source 110 configured to generate a light beam 210 (FIGS. 2a and 2b). The ophthalmic surgical system 100 can include a filter wheel 300 disposed between the light source 110 and an intraocular illumination device 120. The filter wheel 300 can include an unfiltered area 302 (FIGS. 3a-3f) configured to permit transmission of the light beam 210 to the intraocular illumination device 120. The filter wheel 300 can include a first filtered area 304 and a second filtered area 306 (FIGS. 3a-3f) configured to limit the transmission of certain wavelengths of the light beam 210 to the intraocular illumination device 120. The ophthalmic surgical system 100 can include an actuator 220 (FIGS. 2a and 2b) configured to selectively move the filter wheel 300 to cause the unfiltered area 302, the first filtered area 304, and/or the second filtered area 306 to be positioned in a path of the light beam 210 to limit the transmission of the certain wavelengths of the light beam 210.

As shown in FIG. 1, the ophthalmic surgical system 100 can include a light source 110 configured to generate the light beam 210 along a beam path 102. The light source 110 can be, for example, a laser source. The light beam 210 can be split into two, three, or more sub-beams along the beam path 102, between the light source 110 and the filter wheel 300. For example, two, three, or more intraocular illumination devices 120 can be optically or otherwise coupled to the light source 110. The system 100 can include a single filter wheel 300 or include a filter wheel 300 for each sub-beam of the light beam to facilitate filtering of the light going to the intraocular illumination device(s) 120. The light beam 210 along the beam path 102 can be relatively larger than the light beam transmitted to the surgical field by the intraocular illumination device 120. The diameter of the light beam 210 can be between about 10 µm to about 20 mm, between about 200 µm and about 20 mm, or between about 1 mm and about 20 mm, including values such as 1 mm, 2 mm, 3 mm, 4 mm, 5 mm, 6 mm, 7 mm, 8 mm, 9 mm, or other suitable value.

The filter wheel 300 can be disposed between the light source 110 and the intraocular illumination device 120. As described herein in the discussion of FIGS. 3a-3f, the filter wheel 300 can be configured to selectively limit the transmission of one or more wavelength ranges of the light beam 210 along the beam path 102 between the filter wheel 300 and the intraocular illumination device 120. The light beam can be mixed, focused, and/or otherwise processed along the beam path 102 and/or within the intraocular illumination device 120 such that a final output beam of the intraocular illumination device 120 can be homogenous. For example, the diameter of the light beam transmitted to the surgical field by the intraocular illumination device 120 can be between about 1 µm and 500 µm, between about 2 µm and 400 µm, or between about 10 µm and 200 µm, including values such as 5 µm, 10 µm, 15 µm, 20 µm, 100 µm, 200 µm, or other suitable value. Some portion of the beam path 102 and/or intraocular illumination device 120 can include an optical fiber through which the light beam travels.

The ophthalmic surgical system 100 can include an intraocular illumination device 120 configured to operate within a surgical field, such as a patient's eye. The intraocular illumination device 120 can be an optical probe, such as an endoillumination probe, or other device configured to provide light to the surgical field during ophthalmic surgical procedures. For example, the intraocular illumination device 120 can be a chandelier, illuminated cannula entry port, illuminated vitreous cutter, illuminated laser probe, illuminated scissors, illuminated forceps, illuminated pic, or illuminated manipulator.

The ophthalmic surgery system 100 can include a computing device 130 communicatively coupled to the filter wheel 300 and the intraocular illumination device 120. In that regard, to the computing device 130 can be electrically, optically, wirelessly, and/or otherwise communicatively coupled to the filter wheel 300 (or an actuator 220 associated therewith) and/or the intraocular illumination device 120. The computing device 130 can be configured to control and/or monitor the position (e.g., a degree of rotation) of the filter wheel 300. The computing device 130 can also be configured to monitor the position of the intraocular illumination device 120 within the surgical field. For example, the computing device 130 can be configured to track the amount of time, the wavelength ranges, the brightness, and/or other aspects of the light that has been transmitted to the surgical field, including particular areas of the surgical field, such as the macular area, by the intraocular illumination device 120. The computing device 130 can also be configured to provide a signal to move the filter wheel 300 to limit the transmission of certain wavelengths of the light beam 210 along the beam path 102. For example, the computing device 130 can be communicatively coupled to the actuator 220 (FIGS. 2a and 2b) that moves the filter wheel 300. The computing device 130 can provide a control signal to the actuator 220 to rotate the filter wheel 300 such that the light beam 210 along the beam path 102 crosses the unfiltered area 302, the first filtered area 304, and/or a second filtered area 306 (FIGS. 3a-3f).

FIGS. 2a and 2b illustrate various components of the ophthalmic surgical system 100. FIGS. 2a and 2b illustrate a portion of the ophthalmic surgical system 100 between the light source 110 and the intraocular illumination device 120. The filter wheel 300 and the actuator 220 can be disposed between the light source 110 and the intraocular illumination device 120. The actuator 220 can be coupled to and configured to move (e.g., rotate, translate, etc.) the filter wheel 300. The actuator 220 can be configured to selectively move the filter wheel 300 to cause the unfiltered area 302, the first filtered area 304, and/or the second filtered area 306 (FIGS. 3a-3f) to be positioned in the beam path 102 of the light beam 210 to limit the transmission of the filtered wavelengths associated with the first and second filtered areas 304, 306. The actuator 220 can be any mechanism suitable to move the filter wheel 300 such as a brushless DC motor, stepper motor, brushed DC motor, piezo actuator, hydraulic actuator, pneumatic actuator, electric actuator, mechanical actuator, etc. For example, the actuator 220 can include a stepper motor configured to rotate the filter wheel 300. The actuator 220 can be coupled to the filter wheel 300 at an inner edge 312 (FIGS.

3a-3f). For example, a shaft of the actuator 220 can be coupled to the filter wheel 300 at the inner edge 312. Rotation of the shaft of the actuator 220 can cause rotation of the filter wheel 300. The actuator 220 can be coupled to an outer edge 318 of the filter wheel 300. The actuator 220 can be coupled to the filter wheel 300 at one or more locations (e.g., at the inner edge 312 and the outer edge 318, at multiple locations of the inner edge 312, at multiple locations of the outer edge 318, etc.).

The light beam 210 can pass through the filter wheel 300 as shown in FIGS. 2a and 2b. The transmission of one or more wavelength ranges of the light beam 210 can be limited based on whether the light beam 210 passes through the unfiltered area 302, the first filtered area 304, and/or the second filtered area 306 (FIGS. 3a-3f) of the filter wheel 300. The actuator 220 can move the filter wheel 300 (e.g., rotate clockwise or counterclockwise) to cause the light beam 210 to pass through different portions of the filter wheel 300, based on the desired wavelengths of light to be filtered during the ophthalmic surgical procedure.

FIGS. 3a-3f illustrate aspects of the filter wheel 300, including various filtering positions. The filter wheel 300 can include the unfiltered area 302 configured to permit full transmission of the light beam 210, the first filtered area 304 configured to limit the transmission of a first range of wavelengths, and the second filtered area 306 configured to limit a transmission of the second range of wavelengths. Wavelengths of the light beam 210 outside of the first and second filtered wavelength ranges can be allowed to pass through the first and second filtered areas 304, 306, respectively, without being impeded. The first and second ranges of filtered wavelengths can be selected at least partially based on the light source 110 (e.g., the beam composition) of the ophthalmic surgical system 100 and/or wavelengths known to cause damage to the eye, such as blue light wavelengths. Accordingly, the first and/or second range of wavelengths can include wavelengths between about 350 nm and about 520 nm, between about 350 nm and about 515 nm, between about 380 nm and about 480 nm, or other suitable range. For example, the first range of wavelengths can be between approximately 380 nm and approximately 475 nm, and the second range of wavelengths can be between approximately 380 nm and approximately 515 nm.

The first and second filtered areas 304, 306 can be bandpass filters. For example, the first filtered area 304 can be configured to permit wavelengths of the light beam 210 between approximately 475 nm and approximately 650 nm to pass through the filter wheel 300 without being impeded and to limit the transmission of wavelengths outside of that range. Similarly, the second filtered area 306 can be configured to permit wavelengths of the light beam 210 between approximately 515 nm and approximately 650 nm to pass through the filter wheel 300 without being impeded and to limit the transmission of wavelengths outside of that range.

The filter wheel 300 can have a circular or disc profile, as shown in FIGS. 2a-3f. The size of the filter wheel 300 (e.g., height, width, diameter, thickness, etc.), including the areas used to define the unfiltered area 302, the first filtered area 304, and the second filtered area 306, can be selected based on the expected diameter range(s) of the light beam 210. For example, the filter wheel 300 can have a radius 308 between about 10 mm and about 50 mm, between about 12 mm and 50 mm, or between about 12 mm and about 45 mm, including values such as 12 mm, 13 mm, 14 mm, 15 mm, 16 mm, 17 mm, 18 mm, 19 mm, 20 mm, or other suitable value. The filter wheel 300 can also have other configurations, including symmetric, non-symmetric, geometric, and/or non-geometric profiles of various sizes.

The unfiltered area 302 can be positioned adjacent to the first filtered area 304 and/or the second filtered area 306 to allow the light beam 210 to pass at least partially through one or more of the unfiltered area 302, the first filtered area 304, and the second filtered area 306, as discussed below. The unfiltered area 302, the first filtered area 304, and/or the second filtered area 306 can be variously sized and shaped such that a complete diameter of the light beam 210 or any portion thereof can pass therethrough. The unfiltered area 302, the first filtered area 304, and/or the second filtered area 306 can be positioned at any location on the filter wheel 300. Generally, the filter wheel 300 can include any number of filtered areas and any number of unfiltered areas arranged in a suitable manner to facilitate selective filtering of any number of wavelength ranges.

The filter wheel 300 can be made of or include glass, quartz glass, meteoritic glass, germanium, fluorite, plastic, high index plastic, Trivex, acrylic, polycarbonate, or other suitable material. The entirety of the filter wheel 300 can be made of the same material(s) or different portions of the filter wheel (e.g., the unfiltered area 302, the first filtered area 304, and the second filtered area 306) can be made of different material(s). Each of the filtered areas of the filter wheel 300 can be an absorptive or dichroic filter. In that regard, the filter wheel 300 can include one or more optical coatings and/or embedded compounds to define the filtered areas. In that regard, the optical coating(s) and/or embedded compound(s) can be selected and/or applied in a manner to achieve filtering of the desired wavelengths. The optical coating(s) and/or embedded compound(s) can include plastic, metal oxide, zinc sulfide, zinc selenide, sodium aluminum fluoride, natural and/or synthetic dye, organic and/or inorganic dye, colloidal dye, a rare earth transition element, or other suitable material(s). In addition to the optical coatings used for filtering, the filter wheel can include an anti-reflective coating and/or a protective coating. For example, the unfiltered area 302 can include an anti-reflective coating. With the anti-reflective coating, the reflectance of the unfiltered area 302 can be less than or equal to approximately 1.0% of incident light.

Performing an ophthalmic surgical procedure can include guiding the light beam 210 through the filter wheel 300 to the intraocular illumination device 120. The filter wheel 300 can be selectively moved to cause the light beam 210 to pass entirely or partially through the unfiltered area 302, the first filtered area 304, and/or the second filtered area 306 during operation of the ophthalmic surgical system 100. For example, the light beam 210 can be directed at least partially through the unfiltered area 302 when phototoxicity and the Aphakic Hazard metric present less of a concern, such as during surgery on the periphery of the retina. The light beam 210 can be directed at least partially through the first filtered area 304 when phototoxicity and the Aphakic Hazard metric present more of a concern, such as during surgery near the macula. When the second filtered area 306 blocks more wavelengths associated with blue light than the first filtered area 304, then the light beam 210 can be directed at least partially through the second filtered area 306 when phototoxicity and the Aphakic Hazard metric present an even greater concern, such as during extended surgery near the macula.

The transmission of light within the first and/or second wavelength ranges can be limited or attenuated by the first and/or second filtered areas 304, 306 between 0% and 100%. 0% attenuation can occur when the complete diameter of the light beam 210 passes through unfiltered area 302. 100% attenuation within first and second wavelength range can occur when the complete diameter of the light beam 210 passes entirely through the first filtered area 304 or the second filtered area 306, respectively. Attenuation between 0% and 100% can occur when portions of the light beam simultaneously pass through the unfiltered area 302 and at least one of the first and/or second filtered areas 304, 306. The filter wheel 300 can be moved such that the first and/or second ranges of wavelengths of the light beam 210 can be limited in increments of approximately 1%, 5%, 10%, 20%, 25%, 50%, or other suitable value.

In that regard, the filter wheel 300 can be positioned such that a certain percentage of the cross-sectional area of the light beam 210 passes through the filtered area(s) of the filter wheel to achieve a desired amount of filtering. The actuator 220 can be configured to move the filter wheel 300 incrementally to achieve the desired amount of filtering. For example, the actuator 220 can be configured to move the filter wheel 300 in increments such that between about 0% and 100%, between about 0% and 75%, and/or between about 0% and 50% of the cross-sectional area of the light beam 210 can be introduced/removed from the beam path 102 upon each incrementally actuation.

FIGS. 3a-3f illustrate various positions of the filter wheel 300 associated with different amounts of desired filtering. The filter wheel 300 can be moved between the various positions shown in FIGS. 3a-3f by rotating about an axis of rotation 310. The filter wheel 300 can be moved in a clockwise direction 316 and/or a counterclockwise direction 314 about the axis of rotation 310 between the various positions.

Figure 3D:
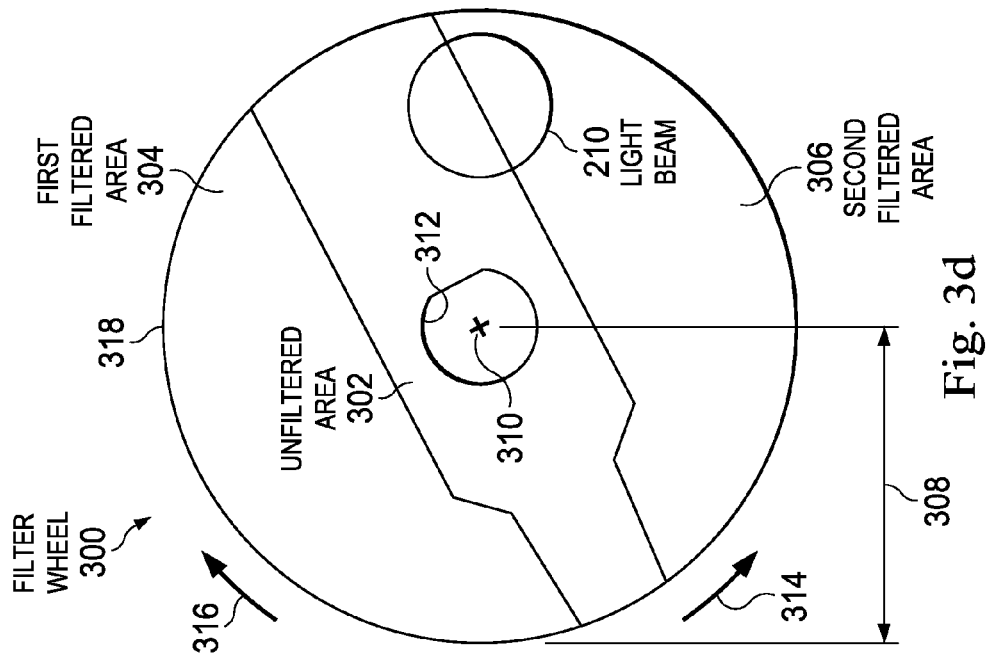
FIG. 3d provides a diagram illustrating an ophthalmic filter wheel.
Figure 3C:
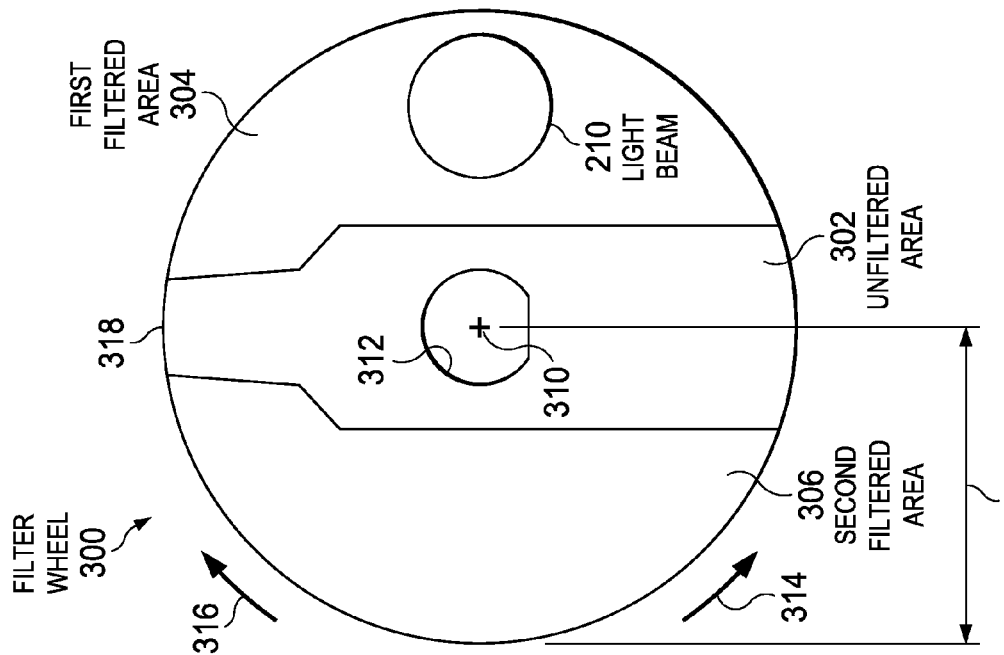
FIG. 3c provides a diagram illustrating an ophthalmic filter wheel.
Figure 3F:
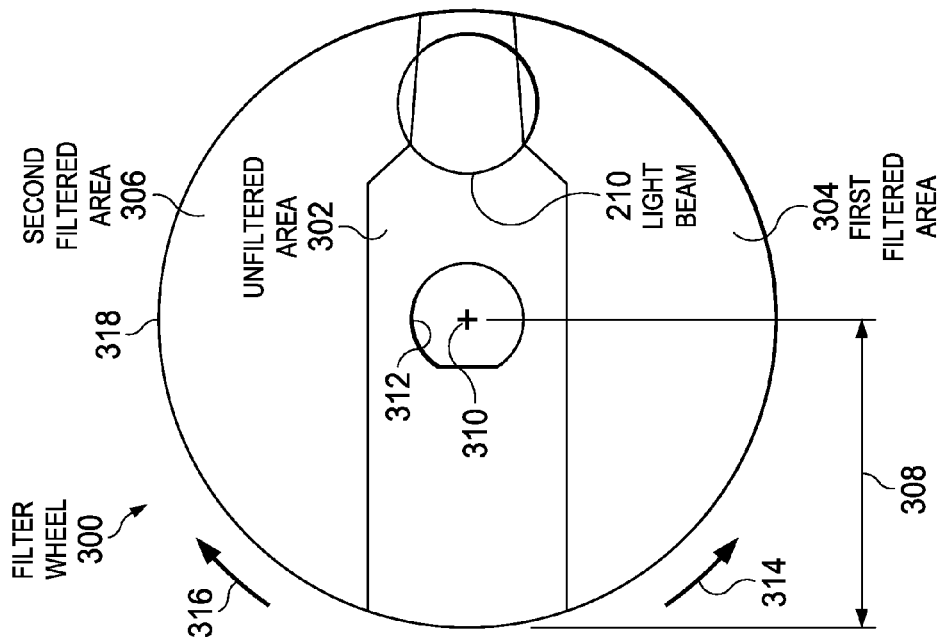
FIG. 3f provides a diagram illustrating an ophthalmic filter wheel.
Figure 3E:
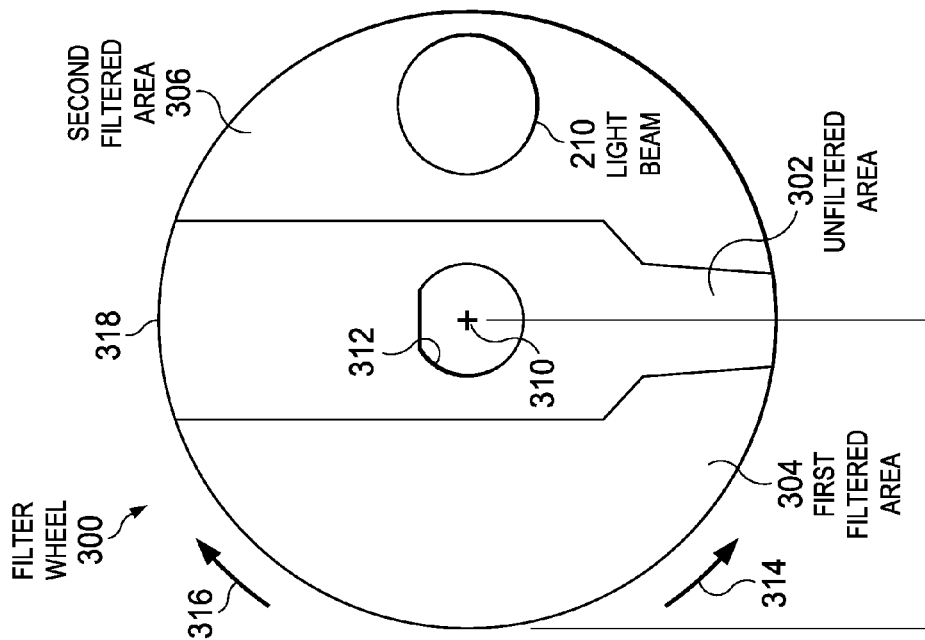
FIG. 3e provides a diagram illustrating an ophthalmic filter wheel.

FIG. 3a illustrates a position of the filter wheel 300 where the entire diameter of the light beam 210 passes through the unfiltered area 302. FIG. 3b illustrates a position of the filter wheel 300 where the light beam 210 passes partially through the unfiltered area 302 and partially through the first filtered area 304 such that the transmission of the first range of wavelengths can be partially limited. FIG. 3c illustrates a position of the filter wheel 300 where the entire diameter of the light beam 210 passes through the first filtered area 304 such that the transmission of the first range of wavelengths can be completely limited by the first filtered area 304. FIG. 3d illustrates a position of the filter wheel 300 where the light beam 210 passes partially through the unfiltered area 302 and partially through the second filtered area 306 such that the transmission of the second range of wavelengths can be partially limited. FIG. 3e illustrates a position of the filter wheel 300 where the entire diameter of the light beam 210 passes through the second filtered area 306 such that the transmission of the second range of wavelengths can be completely limited by the second filtered area 306. FIG. 3f illustrates a position of the filter wheel 300 where the light beam 210 passes partially through the unfiltered area 302, partially through the first filtered area 304, and partially through the second filtered area 306 such that the transmission of the first and second ranges of wavelengths can be partially limited.

The filter wheel 300 can be automatically rotated to position a desired amount of the unfiltered area 302, the first filtered area 304, and/or the second filtered area 306 in the path of the light beam 210 based on one or more conditions associated with the ophthalmic surgical system 100 and/or a surgical procedure. The filter wheel 300 can be moved (e.g., the computing device 130 can provide a control signal to the actuator 220) based on a beam location, a beam composition, an exposure time, and/or a limited visibility condition. The beam location can indicate the target location of the light in the surgical field (e.g., the macula, the periphery of the retina, etc.). For example, if the target location includes the macula, then the filter wheel 300 can be moved such that the light beam 210 passes at least partially through the first or second filtered area 304, 306. The beam composition can describe an amount of blue light included in the light being transmitted to the surgical field. If the light being transmitted includes a potentially harmful amount of blue light, the filter wheel 300 can be moved such that the light beam 210 passes at least partially through the first or second filtered area 304, 306. The exposure time can indicate how long the light has been transmitted to the surgical field. If the surgical procedure lasts for an extended duration such that continued transmission of blue light could be harmful, the filter wheel 300 can be moved such that the light beam 210 passes at least partially through the first or second filtered area 304, 306. A limited visibility condition can describe one or more physiological characteristics of a patient that limit a surgeon's ability to see relevant anatomy during the surgical procedure. For example, cataracts, vitreous hemorrhage, and/or high pigmentation can cause a limited visibility condition. In response, the filter wheel 300 can be moved such that the light beam 210 passes at least partially through the unfiltered area 302.

Embodiments as described herein can relate to devices, systems, and methods that facilitate blue light filtering during ophthalmic surgical procedures. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic surgical system, comprising:
a light source configured to generate a light beam;
a filter wheel disposed between the light source and an intraocular illumination device, the filter wheel including
an unfiltered area;
a first filtered area configured to limit the transmission of a first range of wavelengths of the light beam to the intraocular illumination device; and
a second filtered area configured to limit the transmission of a second range of wavelengths of the light beam to the intraocular illumination device;
an actuator configured to selectively move the filter wheel to cause the light beam to pass through one or more of the unfiltered area, the first filtered area, and the second filtered area of the filter wheel; and
a computing device in communication with the actuator and configured to
monitor the transmission of blue light by the intraocular illumination device within the eye; and
output, in response to the monitoring the transmission of blue light by the intraocular illumination device, control signals to the actuator to limit the transmission of blue light within the eye to minimize retinal phototoxicity by causing the actuator to selectively move the filter wheel such that the light beam passes through one or more of the unfiltered area, the first filtered area, and the second filtered area.

2. The ophthalmic surgical system of claim 1, wherein:
the first filtered area is positioned adjacent to the unfiltered area.

3. The ophthalmic surgical system of claim 2, wherein:
the second filtered area is positioned adjacent to the unfiltered area.

4. The ophthalmic surgical system of claim 3, wherein:
the unfiltered area extends between the first filtered area and the second filtered area.

5. The ophthalmic surgical system of claim 1, wherein:
at least one of the first and second ranges of wavelengths is selected to limit the transmission of blue light to the intraocular illumination device.

6. The ophthalmic surgical system of claim 5, wherein:
the first range of wavelengths includes wavelengths between approximately 380 nm and approximately 475 nm.

7. The ophthalmic surgical system of claim 6, wherein:
the second range of wavelengths includes wavelengths between approximately 380 nm and approximately 515 nm.

8. The ophthalmic surgical system of claim 1, wherein:
the actuator is configured to incrementally move the filter wheel.

9. The ophthalmic surgical system of claim 1, wherein:
the computing device is configured to provide the control signal to the actuator based on at least one of a beam location, a beam composition, an exposure time, and a limited visibility condition.

10. The system of claim 1, wherein the computing device is configured to monitor the transmission of blue light by determining at least one of:
the light beam is directed towards a macula of the eye; or
the light beam is transmitted for an extended duration.

11. A method of performing an ophthalmic surgical procedure, comprising:
guiding a light beam through a filter wheel to an intraocular illumination device, wherein the filter wheel includes an unfiltered area;
a first filtered area configured to limit the transmission of a first range of wavelengths of the light beam to the intraocular illumination device; and
a second filtered area configured to limit the transmission of a second range of wavelengths of the light beam to the intraocular illumination device;
monitoring the transmission of blue light by the intraocular illumination device within the eye; and
selectively moving the filter wheel, in response to the monitoring the transmission of blue light by the intraocular illumination device, to limit the transmission of blue light within the eye to minimize retinal phototoxicity by causing the light beam to pass through at least one of the unfiltered area, the first filtered area, and the second filtered area of the filter wheel.

12. The method of claim 11, wherein:
the filter wheel is selectively moved by an actuator.

13. The method of claim 12, wherein:
the actuator receives a control signal from a computing device.

14. The method of claim 13, wherein:
the computing device provides the control signal to the actuator based on at least one of a beam location, a beam composition, an exposure time, and a limited visibility condition.

15. The method of claim 14, wherein:
the first range of wavelengths includes wavelengths between approximately 380 nm and approximately 475 nm; and
the second range of wavelengths includes wavelengths between approximately 380 nm and approximately 515 nm.

16. The method of claim 15, wherein the selectively moving the filter wheel includes:
positioning the filter wheel such that the light beam passes through the unfiltered area when the light beam is directed to a periphery of the retina;
positioning the filter wheel such that the light beam passes through the first filtered area when the light beam is directed to a macula of the eye; and
positioning the filter wheel such that the light beam passes through the second filtered area when the light beam is directed to the macula for an extended duration.

17. The method of claim 15, wherein the selectively moving the filter wheel includes:
positioning the filter wheel such that the light beam passes through the first filtered area when the light beam is transmitted to the eye for a first duration; and
positioning the filter wheel such that the light beam passes through the second filtered area when the light beam is transmitted to eye for a second duration exceeding the first duration.

18. The method of claim 11, wherein the monitoring the transmission of blue light includes:
tracking at least one of a beam location or an exposure time.

19. The method of claim 18, wherein the monitoring the transmission of blue light includes:
determining the light beam is directed towards a macula of the eye; or
determining the light beam is transmitted for an extended duration.

* * * * *